(12) United States Patent
Lawandy

(10) Patent No.: US 8,961,702 B2
(45) Date of Patent: *Feb. 24, 2015

(54) SUPERCRITICAL FLUID CLEANING OF BANKNOTES AND SECURE DOCUMENTS

(71) Applicant: Spectra Systems Corporation, Providence, RI (US)

(72) Inventor: Nabil M. Lawandy, Saunderstown, RI (US)

(73) Assignee: Spectra Systems Corporation., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,603

(22) Filed: Sep. 9, 2013

(65) Prior Publication Data
US 2014/0116474 A1    May 1, 2014

Related U.S. Application Data

(60) Provisional application No. 61/721,296, filed on Nov. 1, 2012.

(51) Int. Cl.
  *B08B 7/00* (2006.01)
  *A61L 2/18* (2006.01)
  *G07D 7/18* (2006.01)
  *G07D 11/00* (2006.01)

(52) U.S. Cl.
  CPC ............ *A61L 2/18* (2013.01); *B08B 7/0021* (2013.01); *G07D 7/18* (2013.01); *G07D 11/0084* (2013.01)
  USPC ........... 134/31; 134/25.1; 134/34; 134/40; 134/42

(58) Field of Classification Search
None
See application file for complete search history.

(56) References Cited

U.S. PATENT DOCUMENTS

| | | | | |
|---|---|---|---|---|
| 3,708,428 A | * | 1/1973 | McDonald | 510/426 |
| 4,246,295 A | | 1/1981 | Crihan | |
| 4,619,735 A | * | 10/1986 | Norton | 162/135 |
| 5,344,493 A | | 9/1994 | Jackson | |
| 5,370,740 A | | 12/1994 | Chao et al. | |
| 5,401,322 A | | 3/1995 | Marshall | |

(Continued)

FOREIGN PATENT DOCUMENTS

| | | |
|---|---|---|
| CN | 1067584 A | 1/1993 |
| DE | 3904513 A1 | 8/1990 |

(Continued)

OTHER PUBLICATIONS

Lawandy et al., Supercritical Fluid Cleaning of Banknotes, Industrial & Engineering Chemistry Research, 2014, pp. 530-540, 53(2).

(Continued)

*Primary Examiner* — Nicole Blan
(74) *Attorney, Agent, or Firm* — Jeffrey L. Snow; Cooper & Dunham, LLP

(57) ABSTRACT

A method and system for cleaning a secure instrument, such as a banknote, including a substrate, visual data and a security feature, including exposing the secure instrument to a supercritical fluid at a temperature and a pressure and for a duration sufficient to clean the substrate and not compromise the security feature and the visual data, wherein to clean the substrate includes to remove one or more substances from the substrate into the supercritical fluid. The substances removed from the substrate may include contaminants, dirt, sebum and pathogens.

38 Claims, 14 Drawing Sheets

(56) References Cited

U.S. PATENT DOCUMENTS

| | | | |
|---|---|---|---|
| 5,626,821 A | 5/1997 | Kako et al. | |
| 5,881,577 A * | 3/1999 | Sauer et al. | 68/5 R |
| 5,953,780 A | 9/1999 | Schollmeyer et al. | |
| 7,044,376 B2 | 5/2006 | Nelson et al. | |
| 7,820,009 B2 | 10/2010 | Gray et al. | |
| 2004/0076792 A1 * | 4/2004 | Green et al. | 428/96 |
| 2004/0144399 A1 * | 7/2004 | McDermott et al. | 134/1 |
| 2005/0215756 A1 | 9/2005 | Houben et al. | |
| 2007/0122023 A1 | 5/2007 | Jenrick et al. | |
| 2008/0060906 A1 * | 3/2008 | Fitzgerald et al. | 194/207 |
| 2009/0301679 A1 * | 12/2009 | Wetherell | 162/359.1 |
| 2010/0032477 A1 | 2/2010 | Faulkner | |
| 2010/0216686 A1 | 8/2010 | Kobayashi et al. | |
| 2011/0091641 A1 * | 4/2011 | Blankenborg et al. | 427/140 |
| 2011/0200656 A1 * | 8/2011 | Olsson | 424/405 |
| 2014/0299160 A1 | 10/2014 | Lawandy | |

FOREIGN PATENT DOCUMENTS

| | | |
|---|---|---|
| DE | 3904514 A1 | 8/1990 |
| DE | 4004111 A1 | 8/1990 |
| DE | 3906724 A1 | 9/1990 |
| DE | 3906735 A1 | 9/1990 |
| DE | 3906737 A1 | 9/1990 |
| DE | 4200352 A1 | 8/1993 |
| DE | 4344021 A1 | 6/1995 |
| WO | 2007149885 A3 | 4/2008 |
| WO | 2014070307 A1 | 5/2014 |

OTHER PUBLICATIONS

Bender, Moneymakers, Wiley, Apr. 14, 2006, pp. 92, 140-142, 237-239.

Kao et al., Supercritical Fluids as Substitutes for Dry Cleaning Solvents: Evaluation of Enzyme Activity for Stain Removal, Toxics Use Reduction Inst., 1995, 1-13, Report No. 28.

Lawandy et al., U.S. Appl. No. 14/501,145, Systems and Methods for Reversing Banknote Limpness, filed Sep. 30, 2014.

Lawandy, U.S. Appl. No. 14/071,275, Device and Method for Gasochromic Porosity Sensing, filed Nov. 4, 2013.

White et al., Effective Terminal Sterilization Using Supercritical Carbon Dioxide, Journal of Biotechnology, 2006.

LongLife: The banknote paper that "lives" longer, Louisenthal, 2010.

International Search Report for International Application No. PCT/US2013/058775, Feb. 11, 2014.

* cited by examiner before SCCO2 after SCCO2

SUPERCRITICAL FLUID CLEANING OF BANKNOTES AND SECURE DOCUMENTS

CROSS-REFERENCE TO RELATED APPLICATIONS

This application claims priority to U.S. provisional application Ser. No. 61/721,296, filed Nov. 1, 2012.

TECHNICAL FIELD

The present invention relates generally to the cleaning of secure documents such as banknotes without inducing damage thereof. More specifically, the present invention relates to the use of supercritical fluids to clean secure documents or banknotes without damaging their visual data, inks, substrates or security features. The process is also effective in disinfecting the secure documents or banknotes.

BACKGROUND OF THE INVENTION

High security documents such as banknotes have substrates formed from various materials. In the United States, paper currency is made from a non-woven combination of 75% cotton and 25% linen fibers. In most other countries, pulp-based substrates are used. Some countries, such as Canada, have used cotton and paper blended banknotes. In addition, countries such as Australia, New Zealand and Canada have issued banknotes having polymer substrates, e.g., substrates including biaxially oriented polypropylene. The substrate, which may include one or more plies of the substrate material, may include security features such as laminated polymer or paper security threads, planchettes, and watermarks formed directly into the substrate. For example, U.S. paper currency contains small segments of red and blue fibers scattered throughout for visual identification.

Banknotes also include visual data printed on the substrates. The visual data may include images such as portraits, authentication information such as serial numbers, or both. The inks used to print on the substrates may include special dry color pigments blended with oils and extenders and phosphor chips containing layered micro-interference layers. Such inks include Flexo inks, gravure inks, and thicker intaglio inks.

High security documents such as banknotes are generally formed on substrate materials that are frequently equipped with security elements, which are difficult to imitate and which permit even a layman to check the authenticity of the printed information or the document. Security elements can be, for example, windowed security threads, which are visible in certain areas on the surface of the banknote, applied foils, which have a transparent or metallized embossed hologram, blind embossings, so-called "latent images" produced by printing technology or by printing and embossing technology, which render different information from different viewing angles, prints containing optically variable pigments and producing different color effects depending on the viewing angles, and prints comprising metallic effect ink, which have metallic luster, for example, in a gold, silver or bronze tone. In addition to these unaided features, there are quasi-public security threads, fibers and inks, which fluoresce or phosphoresce under illumination with ultraviolet ("UV") or infrared ("IR") sources.

Other security features in paper currency include numeric watermarks, Guilloche patterns, which are narrow geometric patterns created by a geometric lathe or mathematically, microprinting, digital watermarks, magnetic inks and threads, demetalized security threads, holographic features, fluorescent inks, lenticular lens array security threads, and fluorescent and non-fluorescent security threads.

High level covert security features include ENIGMA (De La Rue International) and M (Geiseke and Devrient). An important security feature in currency is the M feature, where "M" refers to "machine readable." The M feature is a colorless, inorganic oxide integrated into the paper substrate, the printing ink, security ink, or a security thread, without causing any change in the appearance of the banknote. The powdered M feature may be blown into the paper substrate in a trail to identify a particular banknote denomination. When exposed to a flash from a strong source of light, the M feature emits a band of light in a split second that rapidly disappears. This repeatable, characteristic light band of the banknote can be authenticated by a reading device. The central banks protect the security of the M feature by requiring the use of special sensors to recognize it.

As counterfeiters have become more sophisticated, the security features in such documents have had to become more advanced as well in order to prevent widespread fraud. As the substrates of such secure documents have become more advanced, the cost to produce them has also increased, thus making the replacement of worn currency quite expensive. Therefore, it is important that in addition to being secure, such documents must have a high level of durability.

Banknotes are removed from circulation for a variety of reasons. Based on one study, 81% of notes are removed because of soiling, 9% are removed because of damage caused by mechanical means, especially tearing, 5% are removed because of graffiti on the notes, 4% are removed because of general wear and tear, and 1% are removed because of damage to the security elements. Generally, 60% to 80% of all rejected bank notes result from to soiling.

Banknotes have a finite time in circulation due to soling and tearing of the notes in use by the public. For example, it takes about 4,000 double folds (first forward and then backward) before a U.S. paper bill will tear. Banknotes are handled in many ways during their usable life and experience a variety of mechanical stresses, as well as being brought into contact with substances that can dirty the notes, resulting in difficulty in their authentication and use. One of the major determinants of the banknote life, which is shortest for the lowest denominations, is soiling. Work by the Dutch National Bank has shown that the primary source of soiling is deposited sebum following contact with fingers, which sebum eventually oxidizes and becomes yellow. Further, a study by the Microbiology Department of Karachi University in Pakistan concluded that currency notes could also carry contaminants that cause diarrhea and urinary tract infections, in addition to skin burning and septicaemic infection. One study found that 26% of notes contained high levels of bacteria, and 80% of notes had some traces of bacteria. An even more concerning finding was that pathogens, including bacteria and viruses, on banknotes have the potential to develop resistance to antibiotics, making the treatment of infectious diseases more difficult.

Such "dirty" money is not simply confined to developing nations. Some of the studies on contaminated currency emerging from the United States were equally revealing. In a recent survey conducted for the Department of Endocrinology at the Wright-Patterson Medical Center in Ohio, researchers collected 68 one-dollar notes from a concession stand at a high school sporting event and a grocery store check-out counter, and examined them for bacterial contamination. Only four bills (six percent) contained no detectable germs.

Given the huge amounts of banknotes in circulation for even small countries, determining the fitness of banknotes is not only of importance in cost control, but also poses a serious technical challenge in terms of processing speed and accuracy. Moreover, the extent of dirtiness of a banknote cannot easily be captured in objective rules. As a result, not only is accurate determination of the fitness of banknotes of interest from a cost point of view, but also cleaner notes are more secure and more attractive to the public. Studies have shown that soiling is one of the primary reasons for classifying banknotes unfit for circulation by banknote fitness sensors using both white light and specific wavelength sources.

In order to improve durability and soil resistance of these substrates, it is known to use documents of value with a dirt-repellent and/or moisture resistant protective layer to extend the documents' lifetime and fitness for circulation. Such a protective layer typically contains cellulose ester or cellulose ether for the greater part and micronized wax for a lesser part, and is applied all over the banknotes. The micronized wax is dispersed by kneading or mixing with oil, an ink binder or a mixture thereof. The sheets freshly printed with the protective layer can be stacked without difficulties and without any black ink from one sheet staining the sheet below.

Another coating composition containing only a binder and no fillers has been applied to the banknote paper, which has a large surface area or high surface roughness due to its porosity. The composition is applied in a layer and has a thickness with a smooth surface, thus having little possibility for resulting dirt deposits. Further, the coating is thin enough not to impair the other stated properties of the paper.

A problem with this approach is that known protective layers do not last or wear well. Conventional protective layers comprising water-based lacquers usually fail to completely meet a demanding requirement profile. For example, very good dirt repellence and adhesion qualities contravene resistance to the penetration of liquid, and vice versa. Water-based lacquers, therefore, currently meet the high requirements for a protective layer in security printing, and in particular banknote printing, only if a second component in the form of a crosslinking agent is added.

Another problem relating to banknotes is that central banks need to replace worn and soiled notes at a cost to taxpayers. In the United States, the volume of notes manufactured is in the billions of notes per year (4-6 billion typically). The production of banknotes is costly, particularly so for the higher denominations, which have many security features that are both accessible to the public and machine readable by bill acceptors and the central banks using high speed sorters. Banknote sorters made by Geiseke and Devrient, De La Rue International and Toshiba typically process banknotes at rates of 10-40 banknotes/second and perform a number of diagnostics using sensors in the notes' travel path. These sensors are a combination of authentication sensors as well as note fitness sensors. The fitness sensors primarily use imaging and analysis of the captured images to determine if the banknote should be destroyed or returned to circulation.

The cost of replacing banknotes is significant as the higher denominations contain Level I, II and III security features for use by the public, commercial banks, single note acceptor devices and central banks. In the United States, for example, the currency replacement budget is $747 million and breaks down as follows:

$1 and $2 notes—5.2 cents per note
$5 and $10 notes—8.5 cents per note
$20 and $50 notes—9.2 cents per note
$100 note—7.7 cents per note
$100 note to be released in October 2013—13 cents per note With over 150 billion new banknotes being manufactured and printed every year around the world, the cost of replacement of unfit currency has approached $10 billion annually. In addition to the replacing the notes, there is a sizable waste disposal cost associated with the destruction of the shredded notes that are determined to be unfit. This amounts to about 150,000 tons of waste worldwide annually, based on total worldwide circulation of 150 billion notes. This is particularly problematic for polymer notes, which also pose larger environmental problems with respect to burning and landfill disposal.

Based on these facts, there is a need to employ a manner for cleaning banknotes, which are soiled but not torn or ripped, that does not attack the print and security features of the note. There is still a further need for a system that applies a certain class of fitness parameters to cause identified banknotes to be cleaned using a method that does not attack the print and security features before making a determination that they should either be returned to circulation or destroyed.

SUMMARY OF THE INVENTION

It is an object of the present invention to provide a method and system to clean banknotes that are soiled but not torn or ripped, which method does not attack the print and security features of the banknotes. It is a further object of the present invention to provide a system that applies a certain class of fitness parameters to cause identified banknotes to be cleaned using a supercritical fluid that does not attack the print and security features of the banknotes before making a determination that they should either be returned to circulation or destroyed.

In general, in one aspect, the invention features a method for cleaning a secure instrument including a substrate, visual data and a security feature, including exposing the secure instrument to a supercritical fluid at a temperature and a pressure and for a duration sufficient to clean the substrate and not compromise the security feature and the visual data, wherein to clean the substrate includes to remove one or more substances from the substrate into the supercritical fluid.

Implementations of the invention include one or more of the following features. The visual data may include an image, authentication information, or both. The one or more substances may include contaminants, dirt, sebum, pathogens, or any combination of these. At least one of the one or more substances may be soluble in the supercritical fluid.

The exposing may further include flowing the supercritical fluid through and around the secure instrument. The flowing may include agitating the secure instrument in the supercritical fluid, agitating the supercritical fluid, and applying ultrasonic waves through the supercritical fluid. The cleaning may include disinfecting. The supercritical fluid may include $CO_2$, and may further include an ionic liquid or another gas.

The method may further include determining the fitness of the secure instrument. The determining for fitness may include scanning the secure instrument to obtain information regarding one or more properties of the secure instrument, and determining whether the one or more properties satisfy one or more predetermined criteria. The predetermined criteria may include an acceptable level of tearing, an acceptable level of limpness, an acceptable level of graffiti, and an acceptable level of soiling. The method may further include authenticating the secure instrument.

The method may further include introducing a trapping material into the supercritical fluid to remove at least a portion of the one or more substances from the supercritical fluid. The trapping material may include a high surface area material, which may include fumed silica. In the method, the duration may be from 30 minutes to 12 hours.

In general, in another aspect, the invention features a method for cleaning a plurality of secure instruments, each secure instrument including a substrate, visual data and a security feature, including sorting the secure instruments based on one or more predetermined criteria, exposing the secure instruments to a supercritical fluid at a temperature and a pressure and for a duration sufficient to clean the substrates and not compromise the security features and the visual data of the secure instruments, wherein to clean the substrates includes to remove one or more substances from the substrates into the supercritical fluid.

Implementations of the invention may include one or more of the following features. The sorting may include scanning the secure instruments to determine whether one or more properties of the secure instruments satisfy the one or more predetermined criteria. The method may further include recirculating the supercritical fluid.

In general, in another aspect, the invention features an apparatus for cleaning a secure instrument including a substrate, visual data and a security feature, including a chamber containing a supercritical fluid at a temperature and a pressure and for a duration sufficient to clean the substrate and not compromise the security feature and the visual data of the secure instrument, and a structure for holding the secure instrument in the chamber so that the supercritical fluid circulates through and around the secure instrument to remove one or more substances into the supercritical fluid.

Implementations of the invention may include one or more of the following features. The apparatus may include an agitation mechanism for circulating the supercritical fluid through and around the secure instrument in the chamber. The structure for holding the secure instrument may include a tray.

In general, in another aspect, the invention features an apparatus for cleaning a plurality of secure instruments, each secure instrument including a substrate, visual data and a security feature, including a sorter for determining whether the secure instruments have one or more properties that satisfy one or more predetermined criteria, a structure for holding secure instruments that satisfy the one or more predetermined criteria, and a chamber containing a supercritical fluid at a temperature and a pressure and for a duration sufficient to clean the substrates and not compromise the security features and the visual data of the secure instruments, wherein the structure of holding secure instruments is capable of being disposed in the chamber so that the supercritical fluid circulates through and around the secure instruments to remove one or more substances into the supercritical fluid.

In general, in another aspect, the invention features a method for restoring a material containing at least one of an image, paint textures, and print, that includes exposing the material to a supercritical fluid at a temperature and a pressure and for a duration sufficient to clean the material and not compromise the image, paint textures, or print, wherein to clean the material includes to remove one or more substances from the material into the supercritical fluid.

Implementations of the invention may include one or more of the following features. The material may be a document containing print or artwork, including a painting having paint textures. The one or more substances may include contaminants, dirt, sebum, pathogens, or any combination of these. The supercritical fluid may include $CO_2$.

BRIEF DESCRIPTION OF THE DRAWINGS

The above-mentioned and other aspects, features and advantages can be more readily understood from the following detailed description with reference to the accompanying drawings, wherein.

DETAILED DESCRIPTION OF THE PREFERRED EMBODIMENTS

The present invention provides for the cleaning of secure documents such as banknotes using supercritical fluids. More specifically, the present invention provides a method of cleaning secure documents and banknotes using supercritical fluids in a manner that does not damage or otherwise compromise their visual data, inks, substrates or the security features contained therein. The security features and visual data are not compromised if they remain recognizable to the public, or upon machine readable examination, for their intended purpose. The substances that can be removed from the substrates of secure documents include contaminants, dirt, sebum from users' hands, and pathogens including bacteria and viruses. Such cleaning may also have the effect of disinfecting the banknotes. It is estimated that the use of supercritical fluid cleaning will allow for a 10% reduction in the number of banknotes that are replaced annually, while allowing a significant percentage of soiled banknotes to be returned to circulation, thus saving governments worldwide approximately $1 billion annually and reducing the environment impact associated with unfit banknotes. At a 10% reduction in_banknote annual production, the estimated decrease in the carbon footprint is $10^6$ tons of equivalent $CO_2$.

Figure 1:
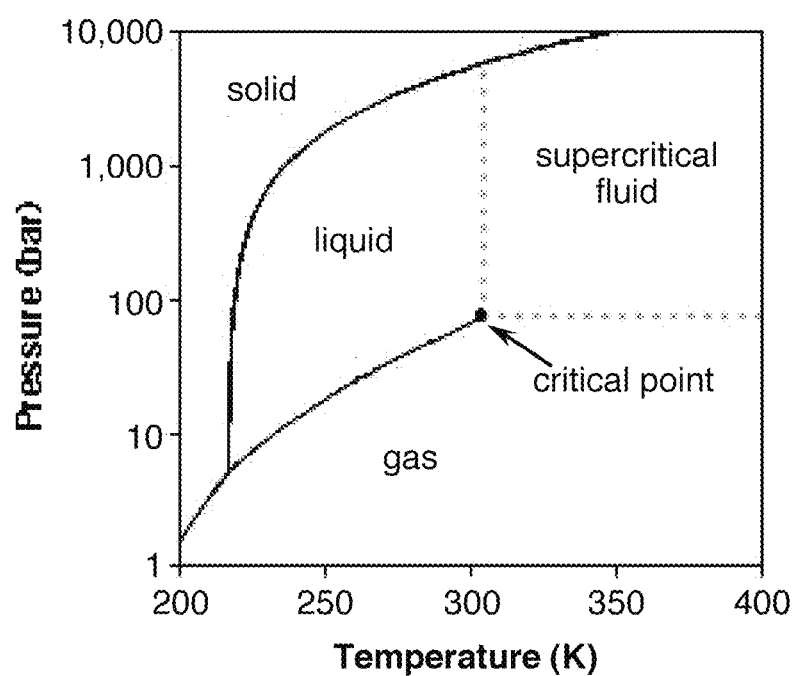
FIG. 1 is a supercritical fluid phase diagram for carbon dioxide.

Supercritical fluids, particularly $CO_2$, mixed with other gases and additives including ionic liquids, are effective solvents for a variety of organics and have been used in a number of cleaning and extraction applications including pharmaceutical manufacturing, perfume production, and decaffeination. The supercritical fluid phase diagram for carbon dioxide is shown in FIG. 1. $CO_2$ has a supercritical point at 72.9 atm and 304.25 K.

When in the supercritical phase, the $CO_2$ material has a density approaching that of the liquid but has the space filling properties of a gas-like substance. When exposed to $CO_2$ in a supercritical state, many organic materials become soluble without chemical attack in certain regions of the phase diagram. In particular, the materials may be removed into the supercritical fluid when their free energy is lowered. In particular, oily substances such as sebum (including after oxidation or hydrolysis), which is a major contributor to banknote soiling, as well as other oils and contaminants, are soluble in supercritical $CO_2$ and other supercritical fluid mixtures. An important point to note is that the banknotes, after this cleaning, are dry since $CO_2$ sublimates at room temperature and pressure. In addition, $CO_2$ as a supercritical cleaning agent has very low environmental impact as one of the lowest impact greenhouse gas components. Any environmental impact associated with the use of $CO_2$ is minimal compared to the cost and negative environmental impact of disposing of unfit currency, e.g., by burning or in landfills. Further, $CO_2$ can be recycled for reuse and recirculation in the cleaning system after filtering out contaminants.

Other supercritical fluids, particularly in trace amounts, may be used in the cleaning system of the present invention. For example, $N_2O$ may be used as a supercritical fluid on its own or in addition to $CO_2$. As a dipolar species, $N_2O$ creates a degree of solubility in the system that cannot be accomplished with $CO_2$ alone. Similarly, CO or $SF_6$ may be used as a supercritical fluid on its own or in addition to $CO_2$. $SF_6$ is particularly useful in a cleaning system because of its highly electronegative properties.

Central banks use high speed sorting machines, which are fitted with optical and mechanical inspection systems that investigate the banknotes to determine if they must be destroyed or can be sent back into circulation. In particular, such high speed sorting machines can be used to interrogate banknotes for both authenticity and fitness. The largest sorting machines operate at 40 banknotes per second and can have as many as 16 sensors to remove counterfeits and notes that are not fit for recirculation. The fitness sensors operate primarily on optical image analysis and examine a number of parameters including tears, tapes, graffiti and soiling. Other sensors may be used to determine banknote limpness as another metric for determining when the notes are fit or have to be replaced. In addition, banknotes may be authenticated to determine whether or not they are counterfeit using the notes' security features, including both public and machine readable security features. Authentication information, which may be machine reasonable, may also be alphanumeric or image data printed on the banknotes.

Figure 2:
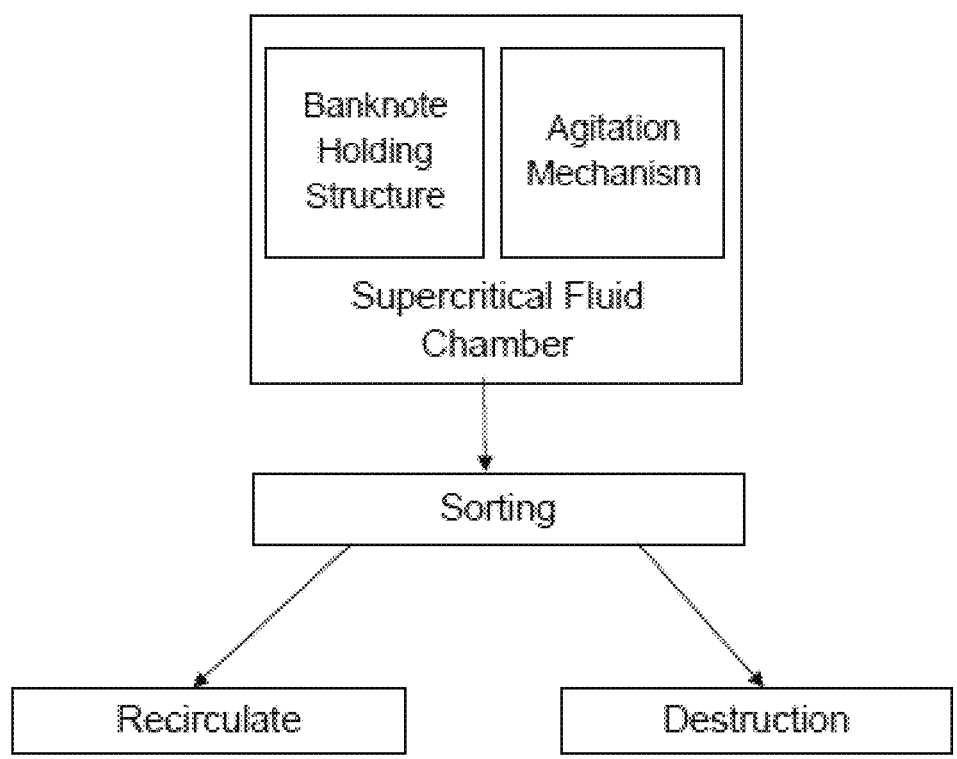
FIG. 2 is a flow chart showing the cleaning and sorting of banknotes in accordance with one embodiment of the present invention.
Figure 3:
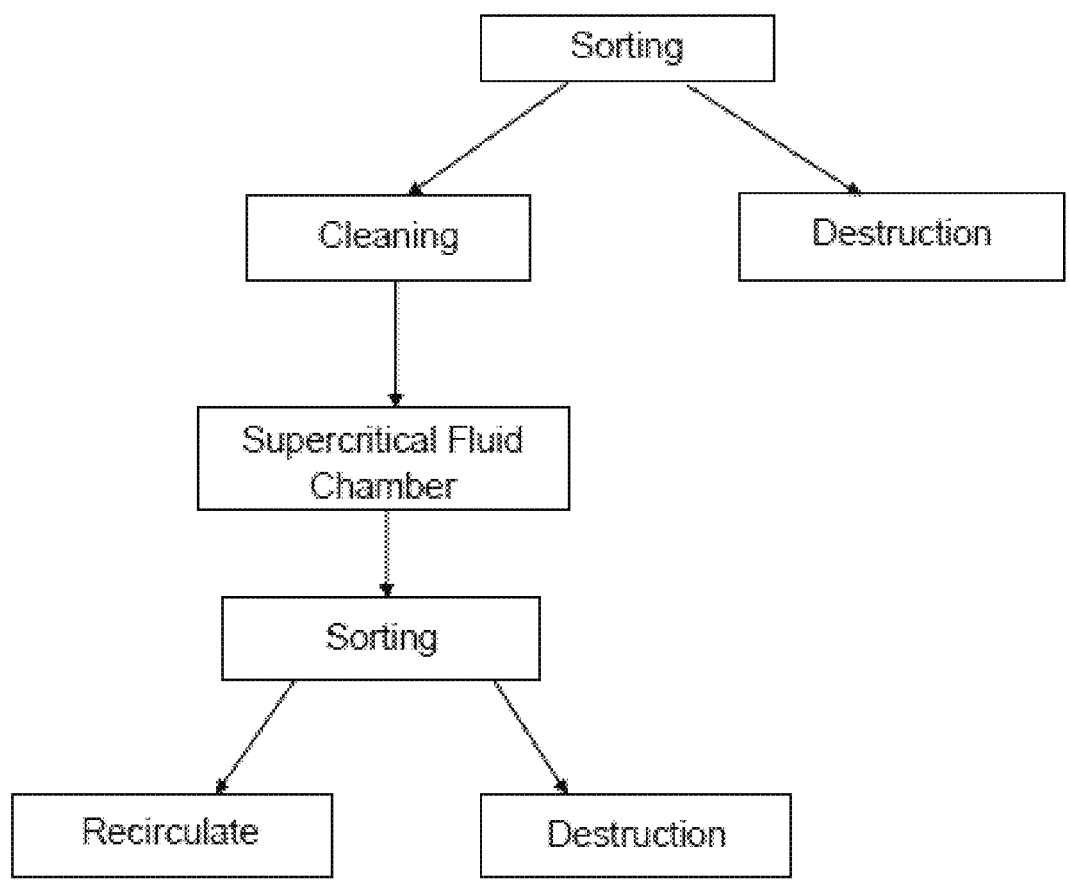
FIG. 3 is a flow chart showing the cleaning and sorting of banknotes in accordance with another embodiment of the present invention.

The present disclosure provides a system for cleaning banknotes including a fitness sensor for analyzing incoming banknotes that selects notes which are unfit due to soiling but are otherwise still viable in terms of limpness and lack of tears, rips and graffiti. These parameters for acceptable fitness characteristics can be determined and optimized by the specific central bank based on population trends and banknote acceptance metrics. In one embodiment, shown in FIG. 2, all banknotes may be cleaned in a supercritical fluid cleaning chamber and then sorted for either recirculation or destruction and/or shredding, depending on whether they meet the predetermined fitness criteria. As shown in FIG. 3, in another embodiment, banknotes that are fit but for their soil level can be routed to a supercritical fluid cleaning chamber. The selected banknotes are placed in the chamber, and supercritical $CO_2$ is applied at an optimal pressure, temperature, and duration for the specific banknote denominations, designs and substrates to remove the soil deposits from the banknote. The required or optimal temperature, pressure and duration will depend on the liquid or liquids in the supercritical fluid, as well as any additions such as ionic fluids or other gases. The cleaned banknotes may then be routed to a second sorting system, which accepts the supercritical fluid-cleaned notes and performs a fitness measurement to qualify those ready for reuse by the public from those that were not successfully cleaned. The latter may be sorted and separated for destruction and/or shredding.

Banknotes that have been sorted or that are otherwise being subjected to the cleaning process of the present invention may be placed in holding structures or trays that may be disposed within the supercritical fluid chamber and that permit the supercritical fluid to flow through and around them to effectuate cleaning. The cleaning process in the supercritical fluid chamber may be further enhanced by the use of an agitation mechanism, which may apply ultrasonic waves through the supercritical fluid, agitate the banknotes (or the structures that hold them), or otherwise agitate the supercritical fluid.

In one embodiment, the banknotes have a thickness of 0.1 mm and can be held in holders or trays separated from each other by a distance of 0.5 mm. Based on this geometry, a supercritical fluid chamber having a volume on the order of 1 $m^3$ can clean over 1 million notes per day. Given that the United States processes 30 billion banknotes each year, supercritical fluid chambers having a volume on the order of 100 $m^3$ would be able to clean all processed U.S. currency, even without sorting the notes first.

To prevent the sebum that is stripped from the banknotes from coating the chamber or re-depositing on the banknotes, and to prevent the supercritical $CO_2$ from saturating with the sebum that is in solution, a trapping material may be provided to remove the sebum from the supercritical $CO_2$. While many trapping agents may be employed to strip the sebum from the supercritical $CO_2$ solution, fumed silica is preferably employed. The trapping material helps to prevent saturation of the supercritical fluid, and may be a high surface area material to which the contaminants may attach. Fumed silica is a synthetic, amorphous, colloidal silicon dioxide. It is produced by the vapor hydrolysis of chlorosilanes, such as silicon tetrachloride, in a hydrogen-oxygen flame at 1800° C. In the combustion process, molten spheres of amorphous silica are formed. Fumed silica is a white fluffy powder, consisting of spherically shaped primary particles, ranging in average from 7 to 40 nanometers in diameter, with a surface area of 400 to 50 square meters per gram. Primary particles do not exist in isolation; they form aggregates and agglomerates. Technical properties of the fumed silica are not just determined by the primary particles, but also by the agglomerate size distribution. The fumed silica does not have a clearly defined agglomerate size. The particle size distribution becomes wider as the average primary particle size increases and the tendency to form agglomerates is reduced.

During the cleaning process, all of the $CO_2$ employed is preferably captured to prevent its release into the environment. The captured $CO_2$ is further recycled for use in subsequent cleaning processes to reduce the overall environmental impact of the cleaning process. The cleaning process of the present invention minimizes the impact on the environment by reducing the thousands of tons of shredded currency that must be disposed of in a landfill or through burning.

Figure 4:
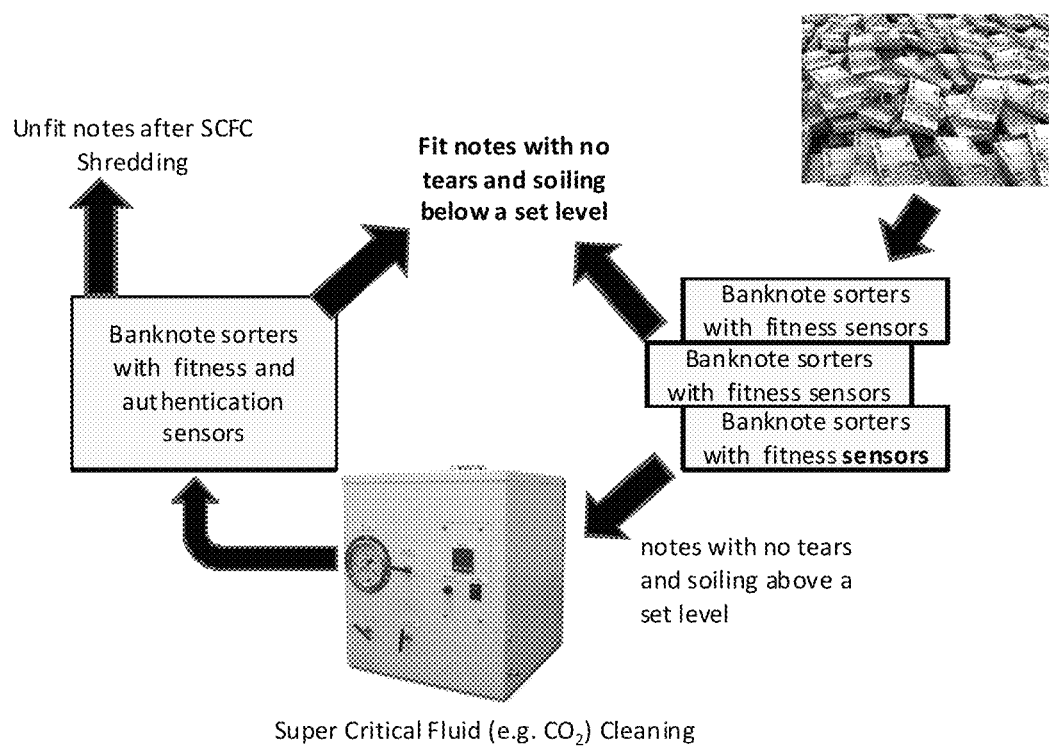
FIG. 4 is a flow chart showing the cleaning cycle of the present invention.

FIG. 4 illustrates the cleaning cycle of the present invention. In an alternate embodiment, a cleaning system may be provided in a cash storage vault that is capable of supporting a supercritical fluid state inside the vault to clean banknotes stored within it. This can be implemented with banknotes that have yet to be processed, yielding a higher yield of notes fit for recirculation after the standard processing by the central bank. Such a supercritical fluid cleaning chamber vault can also be implanted at commercial banks, which may receive a rebate for undertaking this step.

Figure 5:
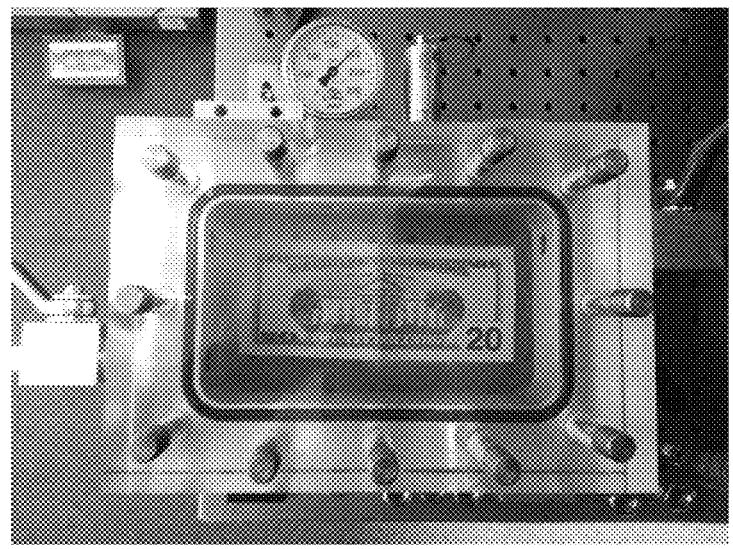
FIG. 5 is an exemplary high pressure supercritical fluid chamber.

Testing was performed on banknotes using a high pressure supercritical fluid chamber. An exemplary chamber is illustrated in FIG. 5, which shows a $20 banknote inside it with $CO_2$ in the supercritical phase. The chamber was made of ¾" aluminum with an observation window made of 1" plexiglass polymer. The chamber was constructed from cold drawn round seamless mechanical tubing (MT-1018) with threaded top and bottom end caps constructed of cold finished AISI C1018 steel bars. The assembled chamber had a diameter of 6.75" and a length of approximately 12.75". The diameter was 5.875", leaving a wall thickness of 0.4375". The chamber had a dual ¼ (npt) threaded fittings machined into the cylinder wall before the cleaning chamber for filling an purging and a second set of ¼ (npt) threads in the top cover for installation of a pressure monitor and a safety release valve. The fabricated components were coated with 0.0001"-0.0003" of electroless-nickel plating for corrosion resistance. The chamber could be operated at temperatures in the range of 25 C and 60 C and at pressures up to 2000 psi, at a duration of 30 minutes to 12 hours. In addition, the chamber could be immersed in an aqueous ultrasonic bath to enhance the cleaning process.

The testing described herein was performed on all notes at the same temperature and pressure. In short, the testing showed that sebum, coffee, and motor oil were removed from the banknotes without compromising the notes' security features. Moreover, in one test, a U.S. $1 note having one colony of micrococcus luteus, a skin bacteria, and 234 colonies of yeast (fungus) was cleaned and disinfected using the method of the present invention, and none of the pathogens remained on the note.

Figure 6:
FIG. 6 is a comparison of the same part of a U.S. $1 banknote before and after coating and oxidation with a sebum layer.

In testing the cleaning process of the present invention, banknotes were coated with a sebum material primarily composed of 18% free fatty acids, 37.8% beef tallow, and 18.3% lanoline. After being coated, the notes were placed in a temperature controlled chamber for 8 days at 90° C. and 65% relative humidity to simulate accelerated aging and circulation of the banknote. After oxidation takes place, the sebum developed a yellowish color, which along with the index matching effects, resulted in a soiled note resembling what is found in circulating currency. For example, FIG. 6 illustrates a side by side comparison of the same part of a new U.S. $1 banknote before and after coating and oxidation with a sebum layer.

Once the notes were soiled, they were cleaned using supercritical $CO_2$ at 50° C. and 1600 psi for 3 to 8 hours. Characterization was aimed at determining the survivability of various ambient light security features viewed under UV light, and machine readable features such as magnetic and high level covert features such as ENIGMA (De La Rue International) and M (Gieseke and Devrient) before and after the cleaning process. The removal of sebum was studied by measuring the diffuse reflectance spectrum and UV features were characterized before and after using a calibrated fluorimeter. In addition, porosity was measured using a photoporousimeter, developed in-house, which allowed for the determination of relative changes caused by the super critical $CO_2$ cleaning process on U.S. banknotes. Pulp based banknotes from the U.S., Europe, and China, as well as polymer banknotes made of biaxial oriented polypropylene coated with an inorganic opacity layer prior to printing, were all tested using these methods.

Figure 7A:
FIG. 7A is images of a U.S. $1 banknote before sebum treatment, after sebum treatment, and after cleaning with a supercritical fluid.
Figure 7B:
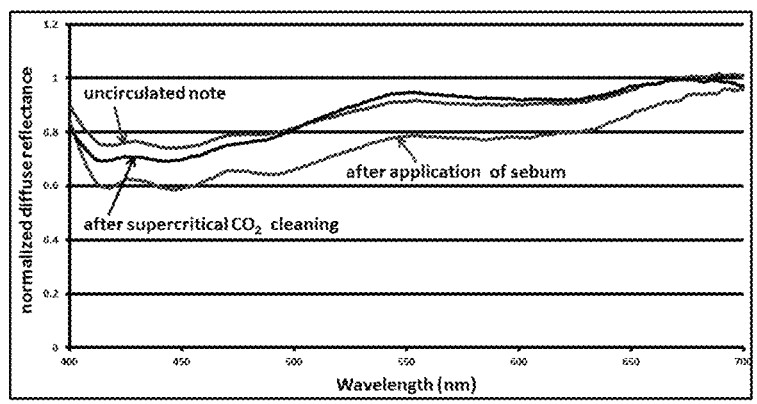
FIG. 7B shows the spectra for each of the U.S. $1 banknote images illustrated in FIG. 7A.

Experiments were performed on a number of banknotes with a focus on U.S. banknotes made from paper which is approximately 75% cotton and 25% linen fibers and printed by the United States Bureau of Engraving and Printing. Results of the cleaning process can be seen in FIGS. 7A and 7B. FIG. 7A illustrates images of a U.S. $1 banknote before sebum treatment, after sebum treatment, and after cleaning with supercritical $CO_2$ at 50 C for 8 hours with ultrasonic agitation. It is important to note that U.S. banknotes include a sebum-like dip which results in a yellowish coloring of banknotes, even when they are brand new. Accordingly, cleaning may not look as efficient at removing all of the sebum as it really is, because of the limitation of the U.S. banknotes. FIG. 7B illustrates the spectra for each of the U.S. $1 banknotes pictured in FIG. 7A. Based on these results, the supercritical $CO_2$ cleaning process effectively removed oxidized sebum from U.S. banknotes. The process removes on the order of 20% of the deposited sebum layer and appears to preferentially remove moieties responsible for absorption in the 500 nm to 650 nm region, which are likely to be the larger fatty acid components of the mixture.

Figure 8:
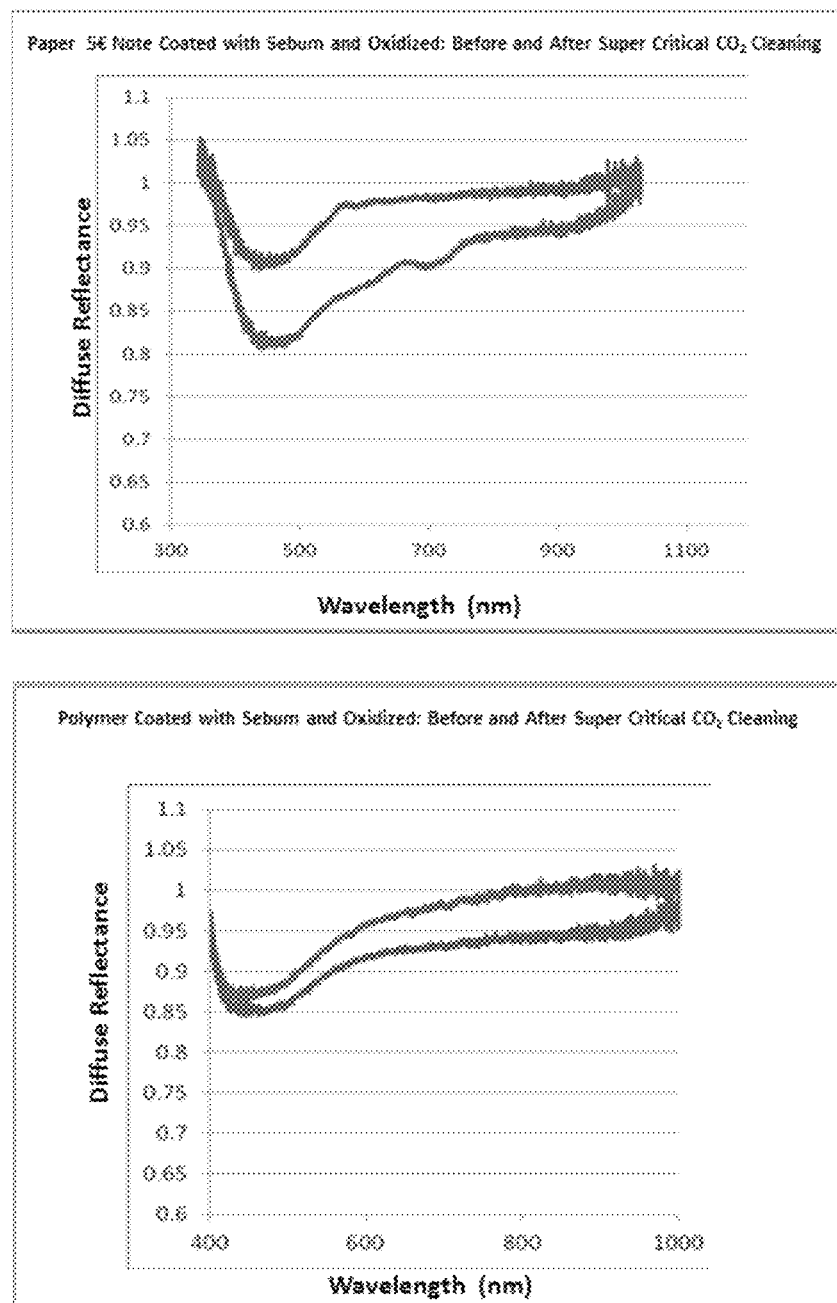
FIG. 8 shows the reflectance spectra of banknotes coated with oxidized sebum both before and after supercritical $CO_2$ cleaning in accordance with the present invention.

The results of the cleaning in this manner can also be seen in the graphs of FIG. 8. Thus, it can be seen that the process disclosed herein cleans a substantial amount of soil from the notes, as evidenced by the nearly 10% increase in the reflectance of the note across the near ultraviolet and visible spectrums. Such cleaning not only enhances the cleanliness and appearance of the note, but also increases the machine readability of the security features on the note.

Figure 9:
FIG. 9 shows the results of cleaning a 5 Euro note in accordance with the present invention.

As seen in FIG. 9, the overall results shown on a 5 Euro note demonstrate clear results of the cleaning process. The left side of the image shows the piece of the note which was cleaned using supercritical $CO_2$ at 1600 psi and 55 C for 8 hours. Before cleaning, the note was coated with Bey sebum and stored at 90 C and 70% relative humidity for nine days.

Figure 10A:
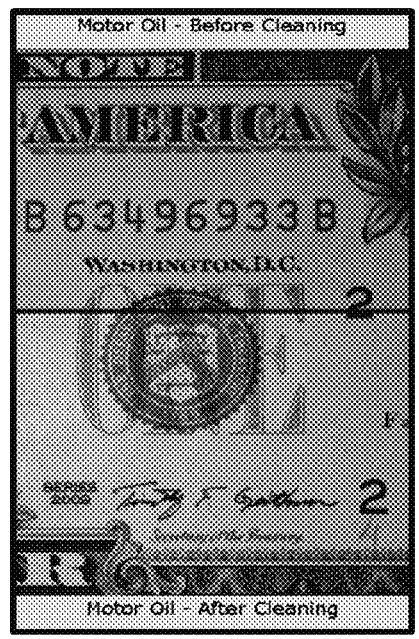
FIG. 10A is a bank note soiled with motor oil before and after cleaning with a supercritical fluid.
Figure 10B:
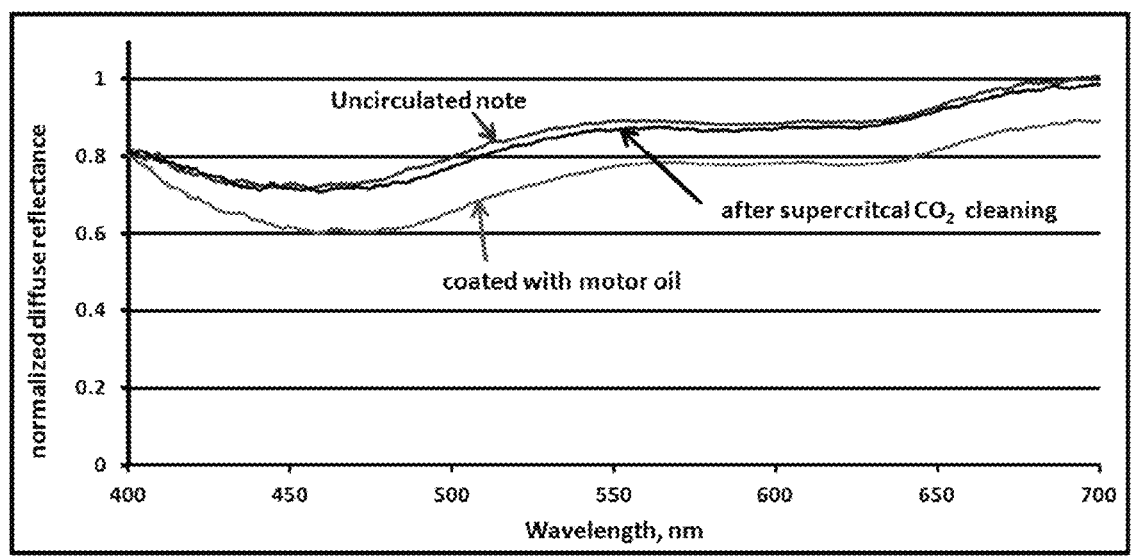
FIG. 10B shows the diffuse reflection spectra of the bank note of FIG. 10A before and after cleaning with the supercritical fluid.

As another demonstration of the effectiveness of supercritical cleaning of banknotes, the process was tested on banknotes soiled with motor oil (e.g., Shell ASE 20). FIG. 10A illustrates a banknote soiled with motor oil before and after cleaning. The images clearly show the efficacy of the cleaning process and the data in FIG. 10B shows the diffuse reflection spectra before and after cleaning.

The key to the viability for recycling of soiled banknotes using these cleaning techniques is dry removal of the oxided oils and other contaminants while maintaining the integrity and usefulness of the important and costly public and machine-readable security features of the banknotes. Optical studies of all the banknotes revealed that no changes in the quality or contrast of the printing were observed after cleaning, including the flexographic, gravure and intaglio and optically variable inks.

Figure 11:
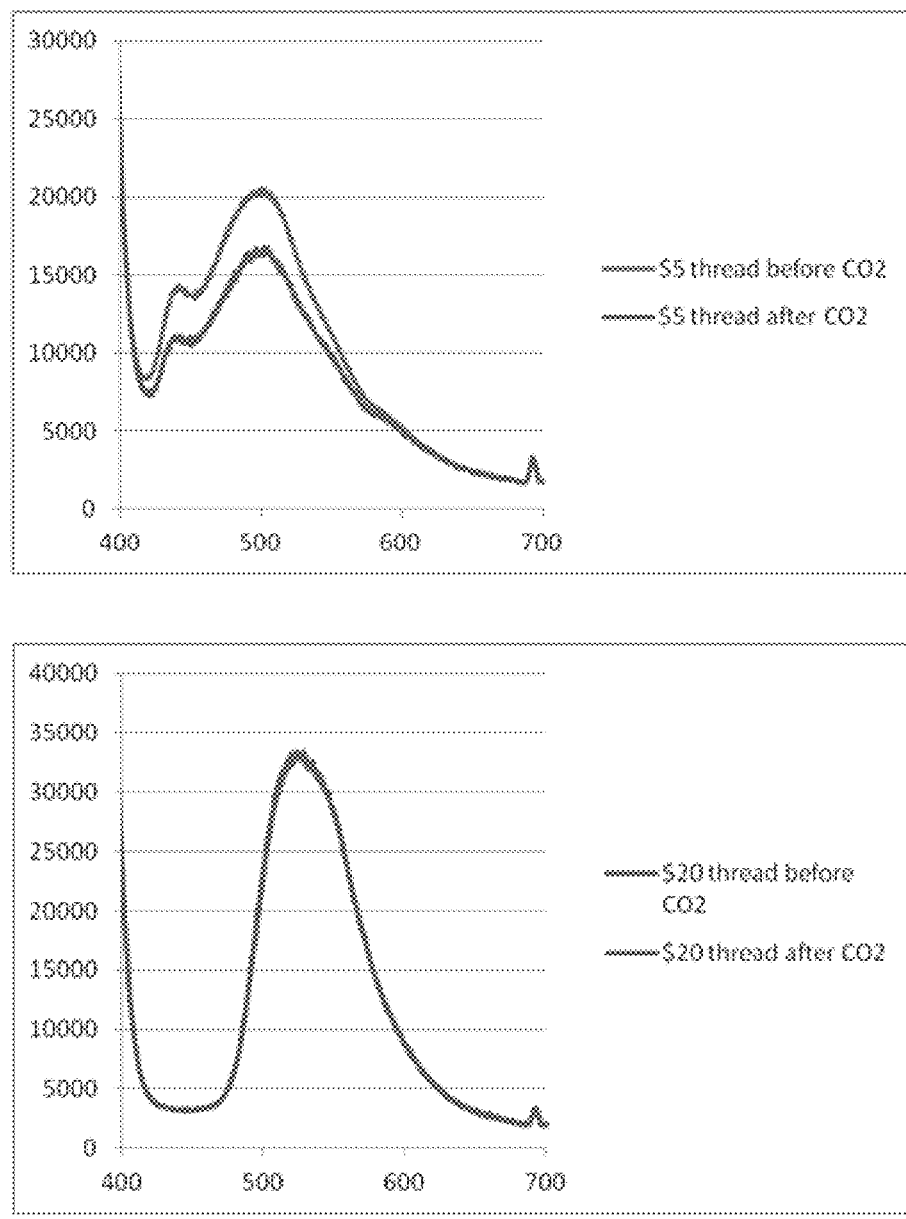
FIG. 11 shows the fluorescence spectra of security threads in banknotes both before and after cleaning in accordance with the present invention.
Figure 12:
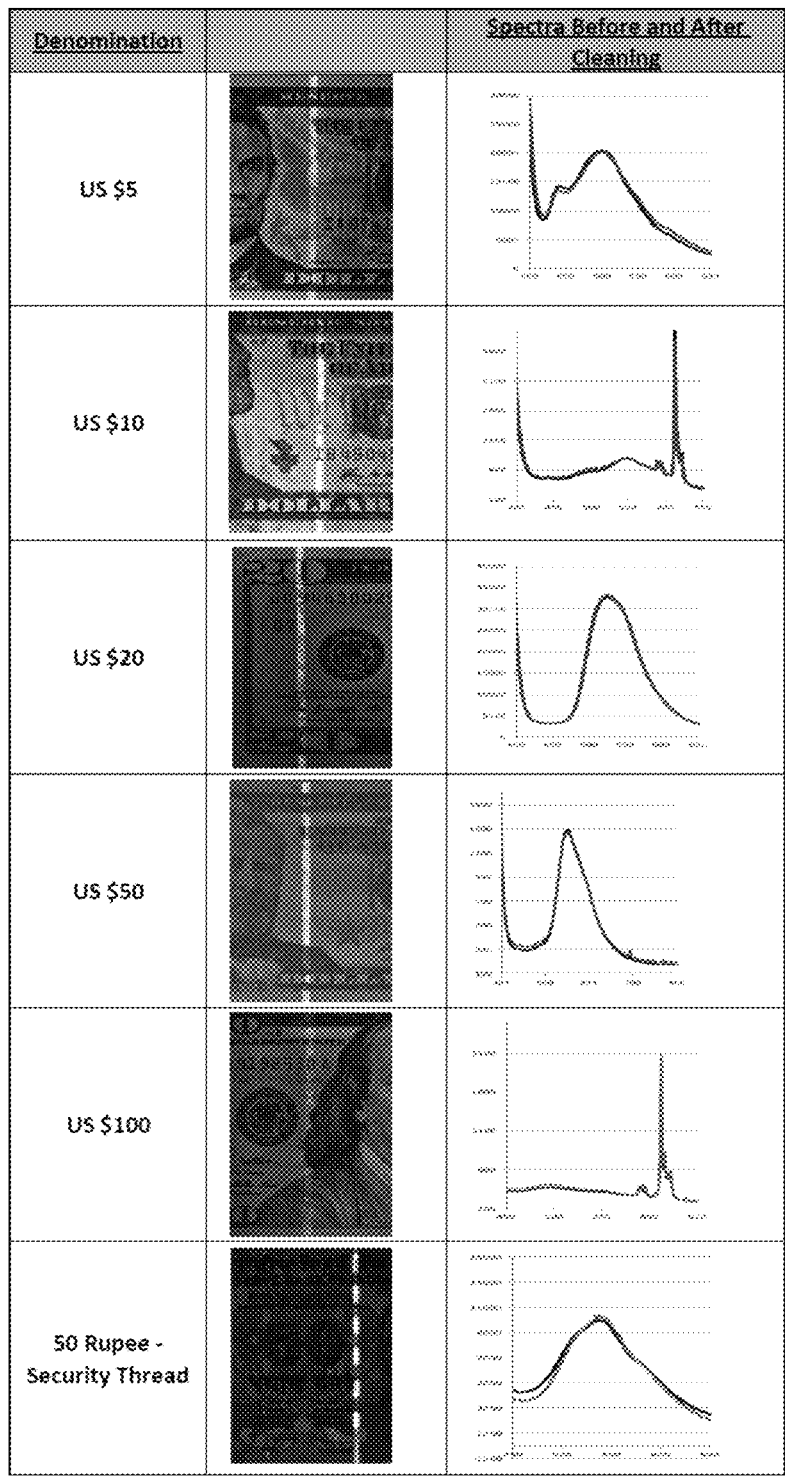
FIG. 12 shows the fluorescence spectra of security threads in banknotes both before and after cleaning in accordance with the present invention.

Another feature of the present invention is that the security features on the bank notes are either totally unaffected or weakly diminished by the cleaning process. Notably, the magnetic inks, fluorescence of UV active features, holograms, metalized and de-metalized threads, and optically variable inks all remain intact and functioning after the cleaning process. As shown in FIG. 11, the fluorescence of the security thread in a U.S. $20 note is wholly unaffected. In addition, the fluorescence of the thread in a U.S, $5 note is slightly reduced after extreme exposure to supercritical $CO_2$; however, the performance is not degraded so as to impair the visual and machine verification process. FIG. 12 shows the fluorescence of security threads in various banknotes, namely U.S. $5, U.S. $10, U.S. $20, U.S. $50, U.S. $100, and 50 Ruppee notes, both before and after cleaning by exposure to supercritical $CO_2$.

Figure 13:
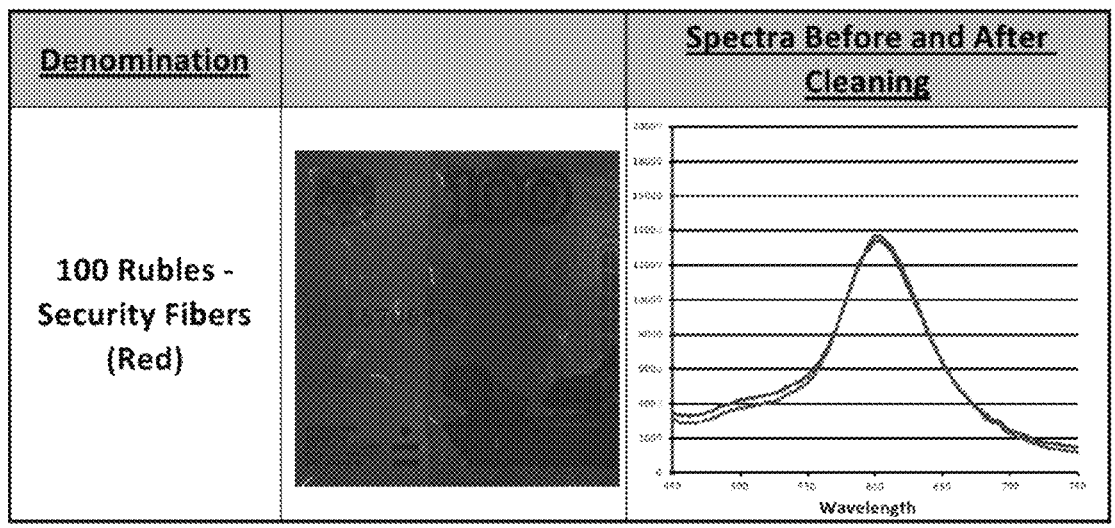
FIG. 13 shows the robustness of the UV excited emissive features in security fibers of a Russian Ruble.

In addition to emissive security threads, polymeric security fibers such as those typically found in many of the world's banknotes were examined. For example, the effects of the cleaning process on the fibers in the Russian Ruble were studied. The data shown in FIG. 13 illustrates the robustness of the UV excited emissive features to the cleaning process with respect to the security fibers in the Russian 100 Ruble banknote.

Figure 14:
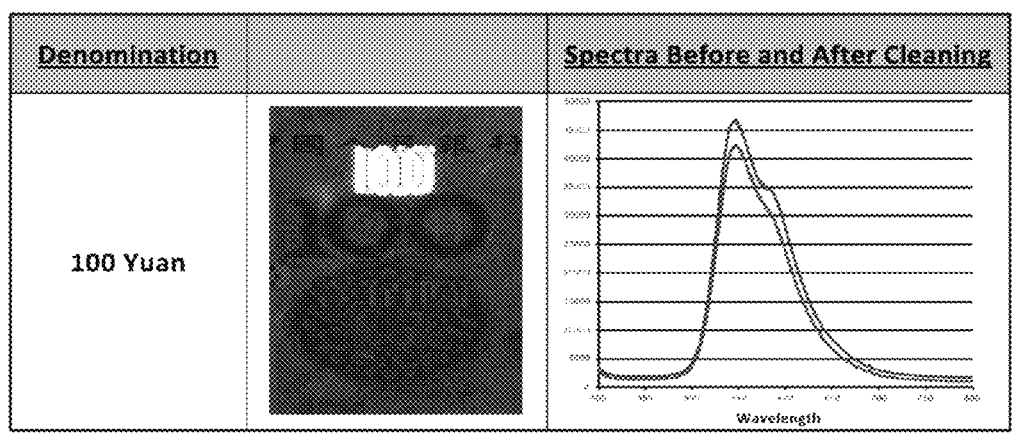
FIG. 14 shows the robustness of the UV excited emissive security features in printing on a Chinese Yuan.

Long UV excited emissive security features are also often printed on a banknote as well using lithographic, flexographic, gravure, and intaglio methods. Examples of this are the Yuan, the Euro, and the British Pound. Printed emissive features in these, as well as other currencies, were studied, and results showed most of them to be highly robust as illustrated by the data for the Chinese Yuan in FIG. 14.

Figure 15:
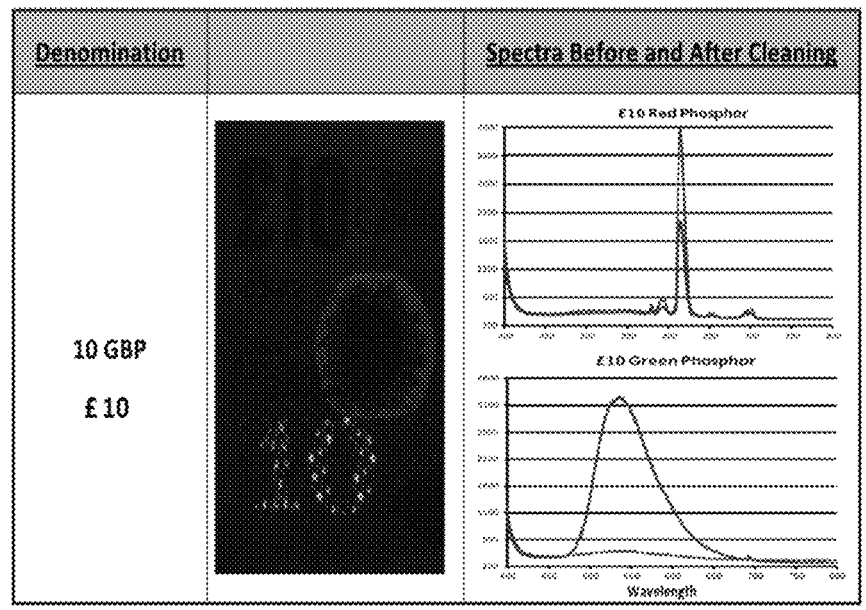
FIG. 15 shows the robustness of the UV excited emissive security features in printing on a British Pound before and after exposure to a supercritical fluid.

Experiments with the UK banknotes, which have a two color UV emissive pattern, revealed that these pigments were partially dissolved away. Experiments using only thermal exposure confirmed that this was either the result of dissolution or reaction with the $CO_2$, and not the thermal degradation of the fluorophore or phosphor. FIG. 15 illustrates the pattern before and after exposure to super critical $CO_2$ at 50 C for 8 hours and the spectral changes that occurred. It is clear from the resilience of the Chinese Yuan example that inks can be formulated to be resilient to the process of cleaning, but that some of the existing ink bases are not.

As previously discussed, machine-readable security features play an important role in banknote security. The most common machine readable security features are based on magnetic and capacitance and are most often utilized in single note acceptor applications from automated teller machines to bill changers and vending machines.

The magnetic inks utilized in a number of banknotes, and particularly the U.S. banknotes and European notes, were found to be robust and unchanged by the supercritical fluid cleaning process at 50 C and for up to 16 hours. Capacitive machine readable features such as those used in security threads, which rely on metallization, also survived testing up to 16 hours.

In addition to the machine-readable features, which are used in the public domain and by commercial banks, central banks employ one or more covert features that are typically read at rates of up to 40 banknotes/sec on high speed sorters. These features are only known to the central banks, the enforcement authorities, and the companies that supply them. One of these technologies is the over thirty year old M-feature, which was developed by Sigreid Otto of Geiseke and Devrient. This security feature proved to be resilient to the supercritical fluid cleaning process as it is based on an inorganic material. Like most of the emissive inks, the key to maintaining its robustness is in the proper choice of the base material if it is in a printed format. The various Enigma security feature signatures from De La Rue International were tested and found to be robust and unchanged after the cleaning process for 16 hours at 50 C.

Another important parameter used to determine the fitness of banknotes is limpness. When banknotes have been in circulation, the mechanical wear from folds, handling, and use in bill acceptors, results in a loss of mechanical elasticity that leads to the notes becoming limp. This "limpness" has been shown to be directly related to changes in the porosity of the banknote with mechanical wear. The porosity of the banknotes increases with use and manifests itself in a lower effective elastic constant. Limpness is measured in automated sorting environments using acoustics and ultrasonic reflection.

The porosity of banknotes was measured to determine the effects of supercritical $CO_2$ and elevated temperatures on the substrate. Supercritical $CO_2$ could cause swelling of the fiber network which could have a hysteresis and leave the banknotes more porous. It is also possible that since paper is a non-equilibrium network, that the relaxed, post-supercritical $CO_2$ treatment could be compacted relative to the initial state.

Figure 16A:
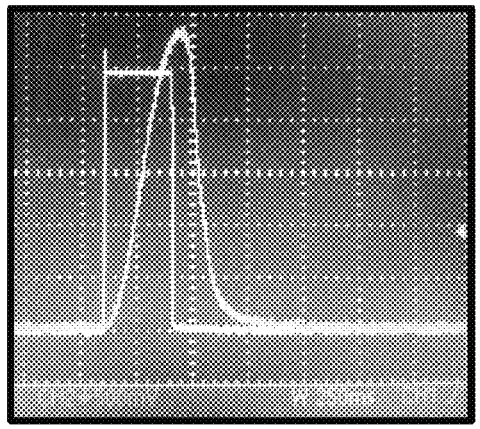
FIGS. 16A and 16B show the transient responses for a U.S. $1 note which is in circulation and which is not in circulation, respectively.
Figure 16B:
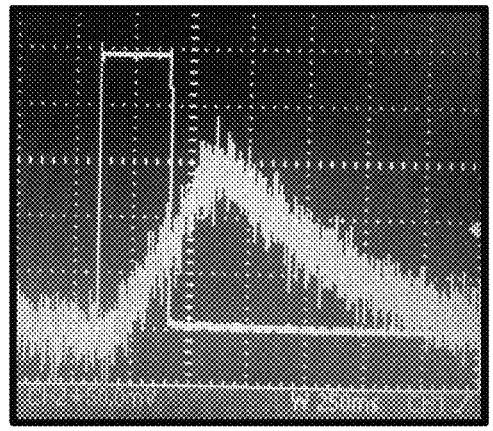
Figure 17A:
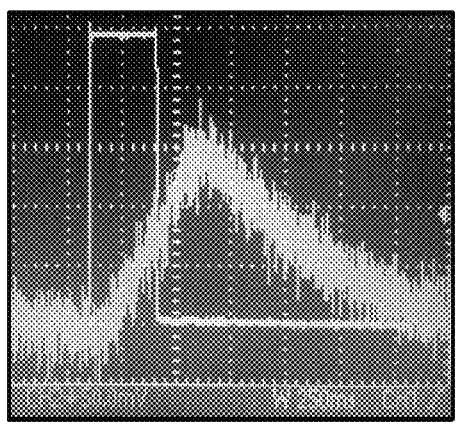
FIGS. 17A and 17B show the signals of the uncirculated note of FIG. 16B before and after cleaning with a supercritical fluid.
Figure 17B:
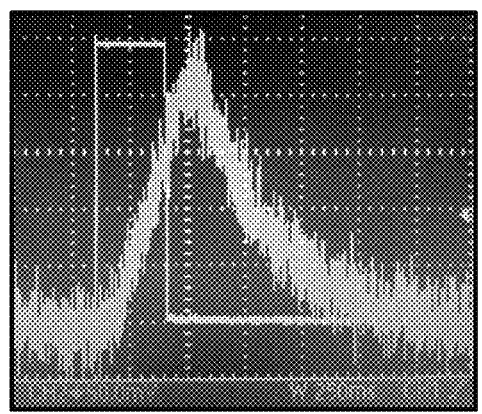

The measurements were made using a home built transient gas diffusion device with Ar as the transport species. The Ar gas was optically detected on the other side of the note. The system utilized a solenoid valve to create a burst of Ar, which was then detected as it diffused through the network. In effect, the delay time was a measure of the void fraction-totuousity product. FIGS. 16A and 16B illustrate the transient responses for a U.S. $1 note, which is in circulation and one that has not been circulated, respectively. The figures demonstrate that the uncirculated note has lower porosity resulting in both a diminished signal and a longer delay relative to the pulse of Ar shown in the yellow trace. FIGS. 17A and 17B illustrate the signals of the uncirculated note before and after supercritical $CO_2$ cleaning and that the process has no effect on the porosity, and hence the limpness, of the note.

The method of cleaning banknotes disclosed herein may also be used to clean and restore other materials that may include images, paint textures, print, or combinations thereof without compromising the integrity of the images, paint textures, and print. The materials may be ones where restoration is desired including, but not limited to documents and artwork, such as paintings. Like the method for cleaning the banknotes, supercritical fluid, such as $CO_2$, may be used to remove substances, including but not limited to, contaminants, dirt, sebum, and pathogens from the material without destroying any images, paint textures, or print that may be on the material.

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. The objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

What is claimed is:

1. A method for cleaning a banknote including a substrate, visual data and a security feature, comprising:
    exposing the banknote to a supercritical fluid at a temperature and a pressure and for a duration sufficient to clean the substrate and not compromise the security feature and the visual data;
    wherein to clean the substrate includes to remove one or more substances from the substrate into the supercritical fluid.

2. The method of claim 1 wherein the visual data comprises an image, authentication information, or both.

3. The method of claim 1 wherein the one or more substances comprise contaminants, dirt, sebum, pathogens, or any combination of these.

4. The method of claim 1 wherein at least one of the one or more substances are soluble in the supercritical fluid.

5. The method of claim 1 wherein the exposing further comprises flowing the supercritical fluid through and around the banknote.

6. The method of claim 5 wherein the flowing comprises agitating the banknote in the supercritical fluid.

7. The method of claim 5 wherein the flowing comprises agitating the supercritical fluid.

8. The method of claim 5 wherein the flowing comprises applying ultrasonic waves through the supercritical fluid.

9. The method of claim 1 wherein to clean comprises to disinfect.

10. The method of claim 1 wherein the supercritical fluid comprises $CO_2$.

11. The method of claim 1 wherein the supercritical fluid further comprises an ionic liquid or another gas.

12. The method of claim 1 further comprising determining the fitness of the banknote.

13. The method of claim 12 wherein the determining for fitness comprises:
    scanning the banknote to obtain information regarding one or more properties of the banknote; and
    determining whether the one or more properties satisfy one or more predetermined criteria.

14. The method of claim 13 wherein the predetermined criteria comprises an acceptable level of tearing.

15. The method of claim 13 wherein the predetermined criteria comprises an acceptable level of limpness.

16. The method of claim 13 herein the predetermined criteria comprises an acceptable level of graffiti.

17. The method of claim 13 wherein the predetermined criteria comprises an acceptable level of soiling.

18. The method of claim 1 further comprising authenticating the banknote.

19. The method of claim 1 further comprising introducing a trapping material into the supercritical fluid to remove at least a portion of the one or more substances from the supercritical fluid.

20. The method of claim 19 wherein the trapping material comprises a high surface area material.

21. The method of claim 19 wherein the trapping material comprises fumed silica.

22. The method of claim 1 wherein the duration is from 30 minutes to 12 hours.

23. A method for cleaning a plurality of banknotes, each banknote including a substrate, visual data and a security feature, comprising:
    sorting the banknotes based on one or more predetermined criteria;
    exposing the banknotes to a supercritical fluid at a temperature and a pressure and for a duration sufficient to clean the substrates and not compromise the security features and the visual data of the banknotes;
    wherein to clean the substrates includes to remove one or more substances from the substrates into the supercritical fluid.

24. The method of claim 23 wherein the visual data comprises an image, authentication information, or both.

25. The method of claim 23 wherein the one or more substances comprise contaminants, dirt, sebum, pathogens, or any combination of these.

26. The method of claim 23 wherein at least one of the one or more substances are soluble in the supercritical fluid.

27. The method of claim 23 wherein the exposing further comprises flowing the supercritical fluid through and around the banknotes.

28. The method of claim 23 wherein to clean comprises to disinfect.

29. The method of claim 23 wherein the supercritical fluid comprises $CO_2$.

30. The method of claim 23 herein the supercritical fluid further comprises an ionic liquid or another gas.

31. The method of claim 23 wherein the sorting comprises scanning the banknotes to determine whether one or more properties of the banknotes satisfy the one or more predetermined criteria.

32. The method of claim 31 wherein the predetermined criteria comprises an acceptable level of tearing.

33. The method of claim 31 wherein the predetermined criteria comprises an acceptable level of limpness.

34. The method of claim 31 herein the predetermined criteria comprises an acceptable level of graffiti.

35. The method of claim 31 wherein the predetermined criteria comprises an acceptable level of soiling.

36. The method of claim 23 further comprising authenticating the banknotes.

37. The method of claim 23 further comprising introducing a trapping material into the supercritical fluid to remove at least a portion of the one or more substances from the supercritical fluid.

38. The method of claim 23 further comprising recirculating the supercritical fluid.

* * * * *